US010213309B2

(12) United States Patent
Lindsey et al.

(10) Patent No.: US 10,213,309 B2
(45) Date of Patent: *Feb. 26, 2019

(54) TISSUE INTEGRATION DESIGN FOR SEAMLESS IMPLANT FIXATION

(71) Applicant: Biedermann Technologies GmbH & Co. KG, Donaueschingen (DE)

(72) Inventors: Ronald W. Lindsey, Houston, TX (US); Zbigniew Gugala, Houston, TX (US); Loren L. Latta, Plantation, FL (US)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/141,394

(22) Filed: Apr. 28, 2016

(65) Prior Publication Data

US 2016/0242912 A1 Aug. 25, 2016

Related U.S. Application Data

(63) Continuation of application No. 10/876,398, filed on Jun. 24, 2004, now Pat. No. 9,364,330.

(Continued)

(51) Int. Cl.
*A61F 2/44* (2006.01)
*A61B 17/70* (2006.01)
(Continued)

(52) U.S. Cl.
CPC .......... *A61F 2/30907* (2013.01); *A61B 17/68* (2013.01); *A61B 17/72* (2013.01);
(Continued)

(58) Field of Classification Search
CPC ............ A61F 2002/3024; A61F 2/2846; A61F 2/30907; A61F 2002/3092;
(Continued)

(56) References Cited

U.S. PATENT DOCUMENTS 3,710,789 A 1/1973 Ersek
3,720,959 A 3/1973 Hahn
(Continued)

FOREIGN PATENT DOCUMENTS

DE 100 07 615 A1 8/2001
EP 1 128 561 A2 8/2001
(Continued)

OTHER PUBLICATIONS

OA issued in U.S. Appl. No. 11/645,228, dated Mar. 17, 2010 (7 sheets).
(Continued)

*Primary Examiner* — David H Willse
*Assistant Examiner* — Javier Blanco
(74) *Attorney, Agent, or Firm* — Lewis Roca Rothgerber Christie LLP

(57) ABSTRACT

The present invention relates to orthopedic implants having a fenestrated hollow shell and a biologic core. These design features provide an improved interface between the implant and the surrounding tissue, aiding fixation, and provide a vehicle for applying new bone healing and enhancing modalities, such as gene therapy, tissue engineering, and growth factors.

28 Claims, 8 Drawing Sheets

Related U.S. Application Data

(60) Provisional application No. 60/482,414, filed on Jun. 25, 2003.

(51) Int. Cl.

| | | |
|---|---|---|
| *A61F 2/30* | (2006.01) | |
| *A61B 17/68* | (2006.01) | |
| *A61F 2/28* | (2006.01) | |
| *A61B 17/72* | (2006.01) | |
| *A61B 17/74* | (2006.01) | |
| *A61B 17/80* | (2006.01) | |
| *A61B 17/86* | (2006.01) | |
| *A61F 2/32* | (2006.01) | |
| *A61F 2/38* | (2006.01) | |
| *A61F 2/40* | (2006.01) | |
| *A61F 2/42* | (2006.01) | |

(52) U.S. Cl.
CPC ....... *A61B 17/7233* (2013.01); *A61B 17/7291* (2013.01); *A61B 17/742* (2013.01); *A61B 17/80* (2013.01); *A61B 17/866* (2013.01); *A61F 2/28* (2013.01); *A61F 2/2846* (2013.01); *A61F 2/30771* (2013.01); *A61F 2/32* (2013.01); *A61F 2/38* (2013.01); *A61F 2/40* (2013.01); *A61F 2/42* (2013.01); *A61F 2/44* (2013.01); *A61F 2002/2835* (2013.01); *A61F 2002/3024* (2013.01); *A61F 2002/3085* (2013.01); *A61F 2002/3092* (2013.01); *A61F 2002/30677* (2013.01); *A61F 2002/30678* (2013.01); *A61F 2002/30784* (2013.01); *A61F 2310/00179* (2013.01); *A61F 2310/00353* (2013.01); *A61F 2310/00359* (2013.01); *A61F 2310/00407* (2013.01); *A61F 2310/00413* (2013.01); *A61F 2310/00592* (2013.01); *A61F 2310/00796* (2013.01)

(58) Field of Classification Search
CPC .......... A61F 2002/30919; A61F 2/4455; A61F 2/446; A61F 2/4465; A61F 2/4475; A61F 2002/448
USPC ............... 623/17.11, 17.16, 23.52, 23.54
See application file for complete search history.

(56) References Cited

U.S. PATENT DOCUMENTS

| | | | |
|---|---|---|---|
| 4,064,567 A | 12/1977 | Burstein et al. | |
| 4,089,071 A | 5/1978 | Kalnberz et al. | |
| 4,492,577 A | 1/1985 | Farris et al. | |
| 4,501,269 A | 2/1985 | Bagby | |
| 4,839,215 A | 6/1989 | Starling et al. | |
| 4,863,474 A | 9/1989 | Brown et al. | |
| 5,108,435 A | 4/1992 | Gustavson et al. | |
| 5,211,664 A | 5/1993 | Tepic et al. | |
| 5,545,222 A | 8/1996 | Bonutti | |
| 5,732,469 A | 3/1998 | Hamamoto et al. | |
| 5,984,926 A | 11/1999 | Jones | |
| 6,015,436 A | 1/2000 | Schönhöffer | |
| 6,126,688 A | 10/2000 | McDonnell | |
| 6,193,755 B1 | 2/2001 | Metz-Stavenhagen et al. | |
| 6,193,756 B1 | 2/2001 | Studer et al. | |
| 6,200,348 B1 | 3/2001 | Biedermann et al. | |
| 6,206,924 B1 | 3/2001 | Timm | |
| 6,245,108 B1 | 6/2001 | Biscup | |
| 6,283,997 B1 | 9/2001 | Garg et al. | |
| 6,319,255 B1 | 11/2001 | Grundei et al. | |
| 6,328,765 B1 | 12/2001 | Hardwick et al. | |
| 6,406,496 B1 | 6/2002 | Ruter | |
| 6,409,764 B1 | 6/2002 | White et al. | |
| 6,746,483 B1 * | 6/2004 | Bojarski ............ A61B 17/0401 623/13.14 |
| 8,702,808 B2 | 4/2014 | Teoh et al. | |
| 8,840,614 B2 | 9/2014 | Mikhail et al. | |
| 2001/0014829 A1 | 8/2001 | Yoon | |
| 2001/0016353 A1 | 8/2001 | Janas et al. | |
| 2001/0018616 A1 | 8/2001 | Schwab | |
| 2002/0068978 A1 | 6/2002 | Camino et al. | |
| 2002/0123750 A1 | 9/2002 | Eisermann et al. | |
| 2002/0138142 A1 | 9/2002 | Castro et al. | |
| 2002/0138144 A1 | 9/2002 | Michelson | |
| 2002/0161441 A1 | 10/2002 | Lang et al. | |
| 2002/0161443 A1 | 10/2002 | Michelson | |
| 2003/0003127 A1 | 1/2003 | Brown et al. | |
| 2003/0014116 A1 | 1/2003 | Ralph et al. | |
| 2003/0040806 A1 | 2/2003 | MacDonald | |
| 2003/0078660 A1 | 4/2003 | Clifford et al. | |
| 2004/0098128 A1 | 5/2004 | Biedermann et al. | |
| 2004/0225360 A1 | 11/2004 | Malone | |
| 2005/0090898 A1 * | 4/2005 | Berry ................ A61F 2/44 623/17.11 |
| 2005/0112397 A1 | 5/2005 | Rolfe et al. | |
| 2005/0234550 A1 | 10/2005 | Metz-Stavenhagen | |
| 2007/0112434 A1 | 5/2007 | Hakamatsuka et al. | |
| 2007/0179610 A1 | 8/2007 | Biedermann et al. | |

FOREIGN PATENT DOCUMENTS

| | | |
|---|---|---|
| FR | 2 548 533 A1 | 1/1985 |
| WO | WO 92/06718 A1 | 4/1992 |
| WO | WO 1998/026725 A1 | 6/1998 |
| WO | WO 98/52498 A1 | 11/1998 |
| WO | WO 01/70135 A2 | 9/2001 |
| WO | WO 02/034168 A1 | 5/2002 |
| WO | WO 2002/071986 A2 | 9/2002 |
| WO | WO 2003/043543 A1 | 5/2003 |
| WO | WO 03/047470 A2 | 6/2003 |
| WO | WO 2004/019827 A1 | 3/2004 |

OTHER PUBLICATIONS

Final OA issued in U.S. Appl. No. 11/845,228, dated Aug. 18, 2010 (8 sheets).

OA issued in U.S. Appl. No. 11/645,228, dated Jan. 9, 2013 (8 sheets).

European Search Report from Application No. 4776952.6 in the name of Biedermann Motech GmbH, European Search Report dated Jul. 9, 2009 and mailed Jul. 16, 2009 (7 pages).

USPTO Office Action dated Jun. 2, 2014 in U.S. Appl. No. 13/914,471 (9 pages).

USPTO Office Action dated Jan. 30, 2015 in U.S. Appl. No. 13/914,471 (7 pages).

OA for Application No. EP 11 181 464.6 dated Jun. 11, 2013 (5 sheets).

USPTO Office action dated Jul. 13, 2016 for U.S. Appl. No. 15/012,827 (12 pages).

USPTO Final Office action dated Oct. 31, 2016 for U.S. Appl. No. 15/012,827 (10 pages).

\* cited by examiner

TISSUE INTEGRATION DESIGN FOR SEAMLESS IMPLANT FIXATION

CROSS-REFERENCE TO RELATED APPLICATIONS

This application is a continuation of U.S. patent application Ser. No. 10/876,398, filed Jun. 24, 2004, now U.S. Pat. No. 9,364,330, which claims priority to U.S. provisional application Ser. No. 60/482,414, filed Jun. 25, 2003, the disclosures of which are incorporated herein by reference.

TECHNICAL FIELD

The present invention relates to the development and use of a mesh-tissue integration implantable device. The implant has the advantages of providing superior fixation and enhanced biological and biomechanical function which increase its longevity relative to conventional implants.

BACKGROUND OF THE INVENTION

Medical and dental implants are widely used today. Typical examples would be the implants used for joint replacements, fractures fixation, and bone reconstruction. Joint replacement implants typically comprise two parts: a metal or ceramic part formed with an articulating surface designed to be received in and rub against a complementary load-bearing plastic surface of either an all-plastic part or a metal part with a plastic surface. In the case of metal implants, the type of metal may include titanium and/or its alloys, or cobalt-chromium and/or its alloys. Other metals useful for medical implants are also applicable. The choice of plastic for the plastic part is, for the most part, ultra-high molecular weight polyethylene (UHMWPE). Fracture fixation and bone reconstruction implants can consist of pins, screws, plates or intramedullary rods. All of these implants require fixation to the bone in order to function properly. The inability to achieve and maintain fixation results in a number of complications which include pain, implant loosening, implant failure, and compromise of function. While the examples discussed focus on medical implants, good fixation stability is an important quality for dental implants also.

The major problem inherent in all implant devices is the gradual loosening over time. This problem is especially prevalent where the implant is subjected to large functional loads and sheer stresses. Cranio-facial implants are particularly prone to this problem. For instance, the difficulty in achieving a dental prosthesis that is strongly bonded to maxillary and/or mandibular bone, and which can withstand large compressive, sheer, and tensile loads has lead to the development of a variety of attachment mechanisms. Many of these mechanisms attempt to adaptively form bone around the prosthesis, with the newly formed bone eventually bonding to the outer surface of the implant. This is especially prevalent for joint prosthesis. As a result of such surface bonding, the fixation stability of these implants is greatest in the weeks directly following implantation, while their useful lives are characterized by a slow loosening or deterioration of fixation stability. It would be desirable to design implants which could retain fixation stability for longer times, and it would be most desirable to design an implant that could actually exhibit improved fixation stability as it ages. Other orthopedic implants such as plates, screws, nails, pins, etc., are also subjected to fixation problems.

A variety of methods for promoting bone formation and attachment have been proposed. For example, U.S. Pat. No. 5,639,237 describes an endosseous dental implant having an indented surface texture for the use in tooth reconstruction. The indented surface increases the surface area for bone contact, thereby enhancing the mechanical fixation and anchoring strength of the dental implant as compared to tooth implants without indentations.

In the case of joint implant, including but not limited to hip, knee, elbow and shoulder, fixation is usually accomplished by the use of cement such as methylmethacrylate, or is achieved by a press-fit method. Both these conventional methods are usually characterized by having the greatest degree of fixation immediately after implantation, but suffer from loss of fixation in the months and years after implantation. Additionally, there is a disadvantage with the use of cements such as methylmethacrylate due to its potential toxicity.

Other approaches have attempted to strengthen the attachment of the bone at the site of the implantation. One such method is taught in U.S. Pat. No. 3,344,654, which claims that a strong bond can be achieved between existing bone and the prosthesis by coating the prosthetic device with an osteogenic protein. To enhance endochondral bone formation, U.S. Pat. No. 5,656,450 teaches compositions and methods for effecting wound healing, specifically the activation of latent growth factor through matrix vesicles. Biodegradable polymeric implants are described which may be prepared containing latent growth factor, matrix vesicles, or matrix vesicle extract. An osteogenic device capable of inducing the formation of endochondral bone when implanted in the mammalian body is also disclosed in U.S. Pat. No. 5,645,591. This device includes an osteogenic protein dispersed within a porous matrix comprising a polymer of collagen and glycosaminoglycan.

Yet another approach for improving the strength and stability of a dental implant is discussed in U.S. Pat. No. 5,383,935. According to the teachings of this patent, a prosthetic device for implantation into skeletal bone generates current flow for calcium phosphate mineral formation between the implant and the surrounding bone. The formation of calcium phosphate minerals at the implant-hone interface is described as encouraging bone attachment to the implant, thereby providing stronger fixation of the implant into the skeletal structure.

An altogether different technique for enhancing bone density at the region of the implant is described in U.S. Pat. No. 5,344,457. This reference teaches effectively transferring loading stress from a dental implant to the surrounding bone through the use of an implant having a tapered body shape. Application of a vertical force on the tapered implant produces a sheer force component in addition to the normal force component acting on the surrounding bone.

Prior to the present invention, various methods have been disclosed in the literature for the attachment of implantable devices to the musculoskeletal system. These methods can generally be classified into those involving impaction grafting, nails and screws, bone cement, and materials with surface ingrowth potential. Interest has recently been focused primarily on implants designed for fixation by tissue ingrowth into the implant's surface as representing a viable solution to the problem of late implant loosening, the most prevalent problem in joint replacement surgery using simple impaction or cementing fixation techniques. There are several types of surface ingrowth materials and methods for their fabrication that have been disclosed in the literature (Pilliar, R. M.: Surgical Prosthetic Device With Porous Metal Coating. U.S. Pat. No. 3,855,638. December, 1974; Pilliar, R. M.: Surgical Prosthetic Device Or Implant Having Pure Metal Porous Coating. U.S. Pat. No. 4,206,516. June, 1980; Smith, L. W. et al; Prosthetic Pans and Methods of Making the Same. U.S. Pat. No. 3,314,420. April 1967; Wheeler, K. R, Supp, K. R., Karagianes, M. T.; Void Metal Composite Material and Method. U.S. Pat. No. 3,852,045, Dec. 3, 1974; Frey. O.: Anchoring Surface For a Bone Implant. U.S. Pat. No. 4,272,855. June, 1981; Spector, M., et al: Prosthetic Devices Having Coatings of Selected Porous Bioengineering Thermoplastics. U.S. Pat. No. 4,164, 794. August, 1979; Homsy. C: U.S. Pat. No. 3,971,670. July, 1976; Tronzo, R.: U.S. Pat. No. 3,808,606. May, 1974; Saner, B. U.S. Pat. No. 3,986,212. October 1976; and Hahn. H.: Bone Implant. U.S. Pat. No. 3,605,123. September 1974). These can generally be grouped into surface ingrowth polymers/ceramics and surface ingrowth metals. As described earlier, the porous polymers offer the advantage of allowing fabrication of a stem with lower rigidity. Their disadvantages are their generally weaker mechanical properties, their poorer biocompatibility, and their much shorter history of clinical use.

Finally, the micro-texturing of the surfaces of orthopaedic implants has been used to increase surface area for better adhesion, as well as promote bone ingrowth into the surface of device. The U.S. Patents of Wagner are exemplary for these methods; see e.g., U.S. Pat. Nos. 6,193,762; 5,922, 029; 5,507,815; and 5,258,098.

Despite the plethora of existing approaches for securing an implanted structure into bone, fixation failures commonly occur. These failures are primarily due to implant loosing caused by the inability of the bone to withstand the physiological loads at the bone/implant interface. One factor in such failures is that the new bone ingrowth surrounding the implant is limited to the surface. Integration of host bone with the implant in a more seamless manner could eliminate this problem and result in better biological and physiological outcomes.

All currently available implants achieve their function by, first, establishing fixation with the host tissue. The inadequate fixation with the host tissue has been one of the major limitations of these devices. The principal components of inadequate fixation include: 1) inadequate bonding with host tissue; 2) non-optimal biomechanical properties; and 3) incompatible biologic properties. With respect to bonding of host tissue, conventional implants have been limited to bonding to the surface of the implant only, with very limited or no tissue ingrowth. Additionally, there is always an interface between the implant and the host tissue, and the interface is always biomechanically and biologically inferior to the implant and host tissue. With respect to biomechanical properties, conventional implants are bulky and stiff in order to offset fatigue, which creates a disparity between the mechanical properties of the implant and the host tissue. This disparity results in stress risers, stress shielding, and bone atrophy. Finally, with respect to the biologic properties, conventional implants either do not support or poorly support tissue biology. These conventional implants are space-occupying devices which alter local tissue biology, do not accommodate the quality of the host tissue, and do not remodel with the host tissue. Additionally, they do not allow for the application of biological factors which could enhance implant function. The result is a biological and biomechanical disparity between the implant and host tissue which culminates in loss of implant fixation.

Thus, there is a need in the medical and dental arts for improving the integrity of fixation of an implant to the host tissue. Coupled with improvements in the biological and biomechanical function, both performance and longevity of implants is possible.

BRIEF SUMMARY OF THE INVENTION

The present invention is directed to an improved musculo-skeletal implant and the methods of making and using the implant. This implant construct will allow for the integration of implant fixation with the host tissue, to adapt continually to the mechanical demands placed on the construct for a permanent living structure.

In one aspect of the present invention, there is a musculo-skeletal implant comprising a fenestrated shell component.

In some embodiments, the musculo-skeletal implant further comprising a biologic core. In some embodiments of the musculo-skeletal implant, the fenestrated shell component comprises titanium. In some embodiments of the musculo-skeletal implant, the fenestrated shell component comprises ceramic material. In some embodiments of the musculo-skeletal implant, the fenestrated shell component comprises cobalt-chromium. In some embodiments of the musculo-skeletal implant, the fenestrated shell component comprises diamond shaped fenestrations. In some embodiments of the musculo-skeletal implant, the fenestrated shell component has a honeycomb pattern, a round pattern, a triangular pattern or any combination thereof. In some embodiments of the musculo-skeletal implant, the biologic core comprises bone tissue. In some embodiments of the musculo-skeletal implant comprising bone tissue, the bone tissue comprises autogenous bone. In some embodiments of the musculo-skeletal implant, the bone tissue comprises musculo-skeletal autografts, musculo-skeletal allografts, musculo-skeletal xenografts, or any combination thereof. In some embodiments of the musculo-skeletal implant, the biologic core comprises osteogenic bone graft substitutes, osteoinductive bone graft substitutes, osteoconductive bone graft substitutes or any combination thereof. In some embodiments of the musculo-skeletal implant, the biological core may be comprised of fibrogenic graft materials, fibruinductive graft materials, fibropromotive graft materials, fibroconductive graft materials, and any combination thereof. In some embodiments of the musculo-skeletal implant, the biological core may be comprised of chondrogenic graft materials, chondroinductive graft materials, chondropromotive graft materials, chondroconductive grail materials, and any combination thereof. In some embodiments of the musculo-skeletal implant, the biological core comprises genetic material. In some embodiments of the musculo-skeletal implant comprising genetic material, the genetic material comprises nucleic acids, plasmids, or vectors. In some embodiments of the musculo-skeletal implant, the biologic core comprises synthetic materials. In some embodiments of the musculo-skeletal implant comprising synthetic materials, the synthetic materials are selected from the group consisting of ceramics, cement, polymers, and combinations thereof. In some embodiments of the musculo-skeletal implant, the biologic core comprises a growth factor. In some embodiments of the musculo-skeletal implant comprising a growth factor, the growth factor comprises a substance which promotes bone growth. In some embodiments of the musculo-skeletal implant, the substance comprises bone morphogenetic protein. In some embodiments of the musculo-skeletal implant, the biologic core comprises a therapeutic agent. In some embodiments of the musculo-skeletal implant comprising a therapeutic agent, the therapeutic agent comprises a drug substance. In some embodiments of the musculoskeletal implant, the implant is a dental implant. In some embodiments of the musculo-skeletal implant, the implant comprises a joint prosthesis. In some embodiments of the musculo-skeletal implant comprising a joint prosthesis, the joint prosthesis is selected from the group consisting of hip implants, knee implants, ankle implants, wrist implants, elbow implants, finger implants, foot implants, toe implants, and shoulder implants. In some embodiments of the musculo-skeletal implant comprising a joint prosthesis, the joint prosthesis is a vertebral implant. In some embodiments wherein the musculo-skeletal implant is a vertebral implant, the vertebral implant is a spinal disk implant. In some embodiments of the musculo-skeletal implant, the implant comprises bone implant hardware. In some embodiments of the musculo-skeletal implant comprising bone implant hardware, the bone implant hardware is selected front the group consisting of bone nails, bone screws, bone rods, and bone plates. In some embodiments of the musculo-skeletal implant comprising bone implant hardware, the bone implant hardware comprises a bone reinforcement implant. In some embodiments of the musculo-skeletal implant, the implant comprises an extracorporeal prosthesis portion. In some embodiments of the musculo-skeletal implant, the implant further comprises a coating of material on at least a part of its surface. In some embodiments of the musculo-skeletal implant comprising a costing of material on at least a part of its surface, said coating material is hydroxyapatite. In some embodiments of the musculo-skeletal implant, the implant further comprising a solid, non-fenestrated portion.

In some embodiments of the musculo-skeletal implant, the fenestrated shell component comprises one or more two-dimensional or three-dimensional fenestrated and, at least partially hollow, mechanical structures, said structures having sufficient integrity to maintain its form against its own weight.

In another aspect of the present invention, there is a musculo-skeletal implant for segmental bone reinforcement, the implant comprising a fenestrated shell component. In some embodiments of the segmental bone reinforcement implant comprising a fenestrated shell component, the implant further comprises a biologic core.

In another aspect of the present invention, there is a method of treating a patient with a musculo-skeletal implant comprising forming an implant having a fenestrated shell component and a biologic core, and implanting the implant into the patient. In some embodiments of the method, the step of implanting the implant comprises implanting the implant intramedullarly, extramedullarly, juxta-osseously, transosseously, or any combination thereof. In some embodiments of the method, the musculo-skeletal implant is a joint prosthesis. In some embodiments of the method wherein the implant is a joint prosthesis, the joint prosthesis is selected from the group consisting of hip, knee, shoulder, ankle, wrist, elbow finger, toe, and foot prostheses. In some embodiments of the method wherein the implant is a joint prosthesis, the joint prosthesis is a vertebral implant. In some vertebral implant embodiments, the vertebral implant is a spinal disk implant. In some embodiments of the method, the musculo-skeletal implant forms at least a portion of a hip, knee, shoulder, ankle, wrist, elbow, finger, toe, or foot prosthesis. In some embodiments of the method, the biologic core comprises material selected from the group consisting of bone material, growth factors, pharmaceutical agents, and a combination thereof. In some embodiments of the method, the musculo-skeletal implant comprises at least one piece of bone implant hardware. In some embodiments of the method, the bone implant hardware is selected from the group consisting of intramedullary fixation devices, pins, screws, plates, vertebral discs, nails, rods, and inserts.

In another aspect of the present invention, there is a method of making a medical implant comprising the step of fabricating a fenestrated shell component from a biocompatible material and loading the fenestrated shell component with a biologically active material.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiments disclosed may be readily utilized as a basis for modifying or designing other structures for carrying out the same purposes of the present invention. This includes: 1) any synthetic device which allows tissue to grow through it to create an integration of tissue and implant device for the purpose of fixing an implant to the tissue; 2) a composite structure of tissue matrix with synthetic reinforcement that creates minimal to zero stiffness mismatch between the host tissue the composite, seamless interface and the implant; 3) a synthetic mesh which can contain a biologic core which, through the mesh, can communicate with and integrate into the living environment into which it is implanted; 4) the location, containment and function of the biologic core is such that any of the current or new "biologic enhancement" material (i.e., bone graft, BMP's, growth factors, genes, calcium phosphates, collagen gels, etc.) can be applied and function through the core. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits or the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

As used herein, "a" or "an" is defined herein as one or more.

As used herein, "core" is defined us the internal space within or in-between a shell component to contain, at least in part, a material that induces or promotes biological activity.

As used herein, the term "fenestrated" is defined as the quality of possessing macroscopic perforations or holes in an otherwise, solid, hollow, or mesh component. In reference to the outer and/or inner shell component of the present invention, "fenestrated" refers to the quality of possessing holes or perforations through which material can grow into or out of the inside of the shell.

As used herein, the term "fenestrated shell component", means a component comprising one or more than one fenestrated shell.

As used herein, the term "implant" is defined broadly, encompassing any and all devices implanted into humans or animals. These include, but are not limited to, orthopaedic implants and dental implants.

As used herein, the term "mesh-tissue integration implant" (MTII) comprises a fenestrated shell component and a biologic core.

As used herein, the term "shell" or "fenestrated shell" is defined as a two- or three-dimensional fenestrated mechanical structure comprising inner and/or outer boundaries for the core.

As used herein the term "tissue" broadly encompasses any and all tissue, including, but not limited to bone and muscle.

The present invention includes a MTII and consists of a radical modification in the basic design of orthopaedic implants. The implant of the present invention exhibits superior integration with the bone of the host, resulting in a seamless or near seamless implant fixation. The enhanced degree of bone integration, relative to conventional orthopaedic implants, results in implants which exhibit superior fixation which improves with time. The present invention also includes the components of the MTII, the fenestrated shell component, and the biologic core.

Figure 1:
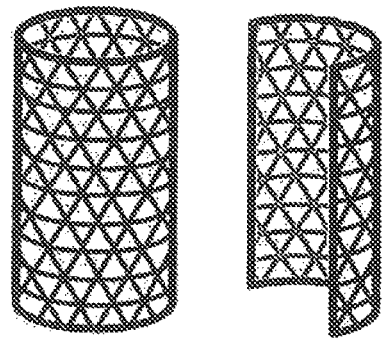
FIG. 1 is a schematic example of the basic single shell design (left); and a view of the same device cut in half along the long axis (right).
Figure 2:
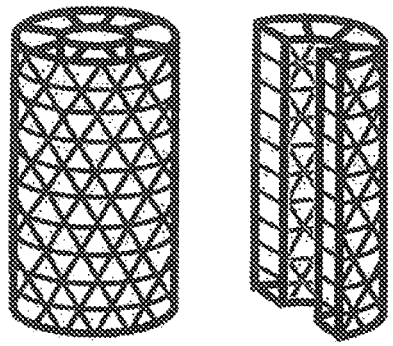
FIG. 2 is a schematic example of a fenestrated shell component design comprising two concentric cylindrical mesh structures (left); and a view of the same device cut in half along the long axis (right).
Figure 3:
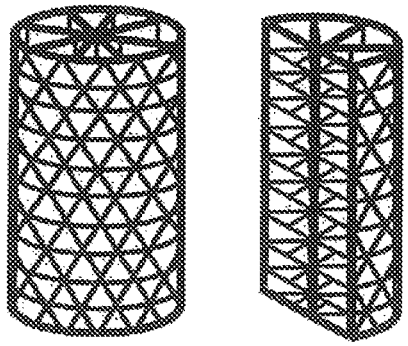
FIG. 3 is a schematic example of a fenestrated shell component having an interconnected three-dimensional design (right); and a view of the same device cut in half along the long axis (right).

There are two integral components of the MTII. These include a fenestrated shell component and a biologic core. The fenestrated shell component may comprise only a single outer shell, or both outer and inner shells which can or cannot be connected with each other. It may also comprise more than two shells. FIGS. 1-3 illustrate some non-limiting examples of the fenestrated shell component. FIG. 1 illustrates one example of a basic design of the fenestrated outer shell component (the left aide of the figure shows the entire device, while the right side illustrates a view of the same device cut in half along the long axis). Although other geometries may be used, the shell of FIG. 1 has triangular fenestrations. FIGS. 2 and 3 illustrate variations on the shell component. The example of FIG. 2 comprises two cylindrical mesh structures (shells) concentrically positioned the left side of the figure shows the entire device, while the right side illustrates a view of the same device cut in half along the long axis). While in FIG. 2 the two shells are integrally connected, this need not be the case in other embodiments. For example, the space between the two shells may be packed with bone graft, cement, or other material. FIG. 3 illustrates an interconnected cylinder (i.e., a 3D mesh) to form a partially filled fenestrated shell component (the left side of the figure shows the entire device, while the right side illustrates a view of the same device cut in half along the long axis). Although the examples in the figures illustrate cylindrical configurations, any single shell need not be cylindrical, and may be any other configuration (oval, triangular, square, rectangular, etc). Additionally, any one or more of the shells in the fenestrated shell component may have a modified surface, such as a teeth-like surface, threads or any other rasp-like surface that promote anchoring into tissue. Many of the potential applications and examples provided which use the MTII can also be performed with only a fenestrated shell component; i.e., the MTII without the biologic core. As will become clear, it is preferable to use a complete MTII, which is the fenestrated shell component and a biologic core.

Figure 4:
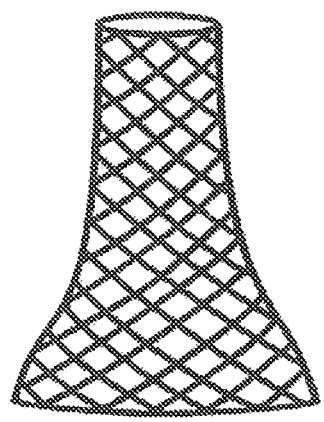
FIG. 4 is a schematic example of a fenestrated shell component having irregular configuration.

Irregular configurations for the fenestrated shell component are also possible. FIG. 4 illustrates an non-limiting example of such a design. Typical natural bone segments are narrow in the middle and somewhat wider at each end. By using an irregular design fenestrated shell implant, one can restore/preserve anatomy. Asymmetric designs, as well as other designs are useful in the present invention. All of the variations discussed in this specification are also applicable to fenestrated shell implants having asymmetric or irregular configurations.

The fenestrated shell component replaces a solid component found in the analogous conventional implants. Preferably, these are made of high-strength materials such as titanium, titanium alloys, although other biocompatible materials (for example, other biocompatible metals, ceramics, or polymers), including those presently used or those yet to be developed in the art of orthopaedic implants are also suitable. These would also include various metal alloys, ceramics, and composite materials. The fenestrated shell component, in combination with the biologic core when present, should have a degree of structural and mechanical integrity, sufficient to tolerate functional loads. At a minimum, this integrity should be appropriate for local loading conditions and local biomechanics of the particular anatomy. The structural and mechanical strength characteristics of the device need not be symmetrical; it could be polarized to match the loading expected. At a minimum, the device should have sufficient integrity to maintain its structure against its own weight, and would preferably maintain its form upon application of small biomechanical loads.

The fenestrations are holes or openings in the wall of the material, resulting in a mesh-like structure which retains sufficient structural integrity and rigidity. This differs from commonly used micro- and macro-texturing techniques, which only roughen/texture the surface of the implant to provide enhanced fixation through increased surface area and surface-limited bone ingrowth. The fenestrations on the wall of the material may be varied in size and geometry for optimal results for the specific implant operation to be addressed. Diamond shaped fenestrations, as well as those having a geometry resulting in u honeycomb pattern on the shell have been used, but other geometries are also useful in the present invention. As non-limiting examples, in addition to honeycomb, the geometries may be round, ellipsoid, triangular, or other shape, and any combination thereof. There may be different sizes and geometries (i.e., not necessarily homogeneous) of the fenestrations on a particular implant. The fenestrated shell component may be comprised of fenestrations of various shapes, slices, and combinations of such. The fenestrated outer and/or inner shell can consist of biocompatible metals, and/or ceramics, and/or polymers with sufficient biomechanical properties and will provide the internal space for a biologic core. The shell will control the loading of the biologic core and, by providing boundaries for the biologic core, will restrict bone formation/reconstitution, within this space. Restricting bone to the predefined space allows one to control the extent and nature of the bone to be formed. Restricting bone formation in this way allows one to tailor the prosthesis to the morphological and functional demands of the local biology. Fenestrations in the shell may have specific sire and geometry to mediate the biologic core's interface with the adjacent tissues and permit the integration with native bone. The fenestrations of the outer and/or inner shell allow for a limited contact of the biologic core with the neighboring/adjacent host tissue (outer shell) and endosteum (inner shell). This contact will permit the nutrition of the biologic core by diffusion of nutrients and vessel ingrowth form the surrounding host tissue.

The fenestrations of the outer and/or inner shell afford enhanced bonding with the host tissue. The mesh qualities of the fenestrated outer and/or inner shell(s) result in a more complete and seamless integration. As tissue grows around the outer and/or inner shell(s), it becomes embedded in the tissue, essentially becoming part of the tissue. Bonding is no longer limited to the surface of the implant as it is in conventional implants. The mesh qualities of the fenestrated shell component result in a more complete and seamless integration. As tissue grows around the shell, it becomes embedded in the tissue, essentially becoming pan of the tissue. Tissue ingrowth is enhanced through the presence of the fenestrations, as tissue can grow through the fenestrations and surround the implant. This "reduction in interface" results in a seamless union and superior bonding to host tissue. This is in stark contrast to conventional implants in which the interface is always biomechanically and biologically inferior to both the bulk of the implant and to the host tissue, particularly with regard to structural integrity. Producing a more seamless interface results in a amelioration of the biological and biomechanical deficiencies which are inherently present at the interface.

The fenestrated shell component design also affords an implant consisting of a minimum amount of foreign body material. This allows the implant to more closely match the mechanical properties of the host tissue and minimizes the appearance of stress risers, stress shielding and bone atrophy. The aforementioned qualities save space relative to conventional implants, better accommodating the host tissue. Importantly, as discussed below, the fenestrated shell component allows for loading of material in the biological core. These materials may be used for beneficial purposes, particularly to enhance implant function.

The other component of the MTII of the present invention is a biologic core. An important function of the biologic core is its ability to house biological factors which enhance the formation and/or maturation of new tissue to provide implant stability, fixation, and function. The biologic core is contained within the fenestrated outer shell, or in-between the outer and inner shell, and/or the inner shell and may consist of any biological material but preferably comprises standard cancellous bone graft or biologically active bone graft substitutes. Where cancellous bone is used, it may originate from a variety of sources, including autogenous bone material or allografts. Allografts, typically but not always, come from cadaver bone. The biologic core allows for the integration of the entire implant or a portion of the implant with the host skeleton. Alternatively, or in combination with other materials, the biologic core may comprise osteogenic, osteoinductive, and/or osteoconductive bone graft substitutes. In this way, gene therapy modalities can be incorporated into the MTII through the use of nucleic acids and/or other genetic materials in the biologic core. Other genetic materials include, but are not limited to, nucleic acids, plasmids, or vectors. Tissue engineering modalities are also enabled in this way, by incorporated natural and synthetic materials into the biologic core. Ceramics, cements, polymers, other useful materials, and combinations thereof, can be used in this regard in the biologic core matrix. Any other drug or chemical that can be released from the core that facilitates the function of the implant is included in this invention.

The biologic core, while ideally suited to contain bone tissue, may also comprise other substances having therapeutic effectiveness. This may include any one or a combination of substances, materials, or factors that promote bone or tissue growth. This could be, for example, bone morphogenetic protein, or any factor that can enhance bona growth. Preferably, the biologic core comprises bone graft or biologically active bone graft substitutes. Where bone is used, it may originate from a variety of sources, including autogenous bone material or allografts or cadaver bone. Additionally, the biologic core may comprise other therapeutic agents, such as pharmaceutical components. A difference between the instant invention and the prior art cages is that the MTII achieves permanent fixation by integration of its interstices with the host tissue; whereas the prior art cages attempt to immobilize/fuse to two or more mobile segments of the host tissue.

Another function of the biological core is to allow for host bone proliferation and/or reconstitution within the implant. This new bone becomes the major component of the implant. It provides strength which is commensurate with the host bone. Additionally, it is capable of sustaining biological characteristics consistent with the host bone. In doing so, the integration of the core and the host bone becomes seamless. The production of a seamless interface will necessarily minimize the inherent deficiencies, structural and otherwise, which are present at the interface.

The fenestrations of the MTII (or in some applications, the fenestrated shell component) are in direct contact with the host bone and serve as an interface to promote the integration of the host bone with the biologic core. This provides for the seamless, integrated union between the implant and the surrounding bone. The degree of bone ingrowth into the implant is greatly enhanced relative to the results obtained using the conventional methods of achieving fixation. In specific embodiments where this is coupled with a biologic core which enhances bone growth, the results are even further improved. This is particularly pronounced where the fenestrated cage is placed intramedullarly, affording close contact with the surface and the fenestrations. The intramedullar implantation can be used in all applications of the present invention, including but not limited to, convention bone implants such as hips, knees, and shoulders, among others.

Although intermedular implantation has certain advantages, it is also within the scope of the present invention to implant these devices extramedullarly, juxta-osseously, trans-osseously or any combination thereof. The skilled artisan will recognize when these other configurations are desirable based on the problem at hand and may use them accordingly.

Another advantage of the present invention is that implantation is amenable to a variety of locations and configurations. The MTII of the present invention can be intramedullar, extramedullar, juxta-osseous, or transosseous. Conventional cage-type implants are limited to interpositional locations such as segmental bone defects or interbody spine fusion.

Hybrid MTII Implants

The present invention is applicable to all conventional implants, including but not limited to hip, knee, ankle, foot, toe, shoulder, elbow, wrist, finger joints, includes vertebral segments, and also includes dental implants such as artificial teeth or posts to anchor the same. The implants of the present invention represent a marked improvement in performance and longevity over conventional implants. The function of all these implants requires implantation (i.e., fixation) into bone tissue. Fixation stability is commonly a problem in all implants, and is typically the implant life-limiting factor that necessitates revisions.

Figure 5:
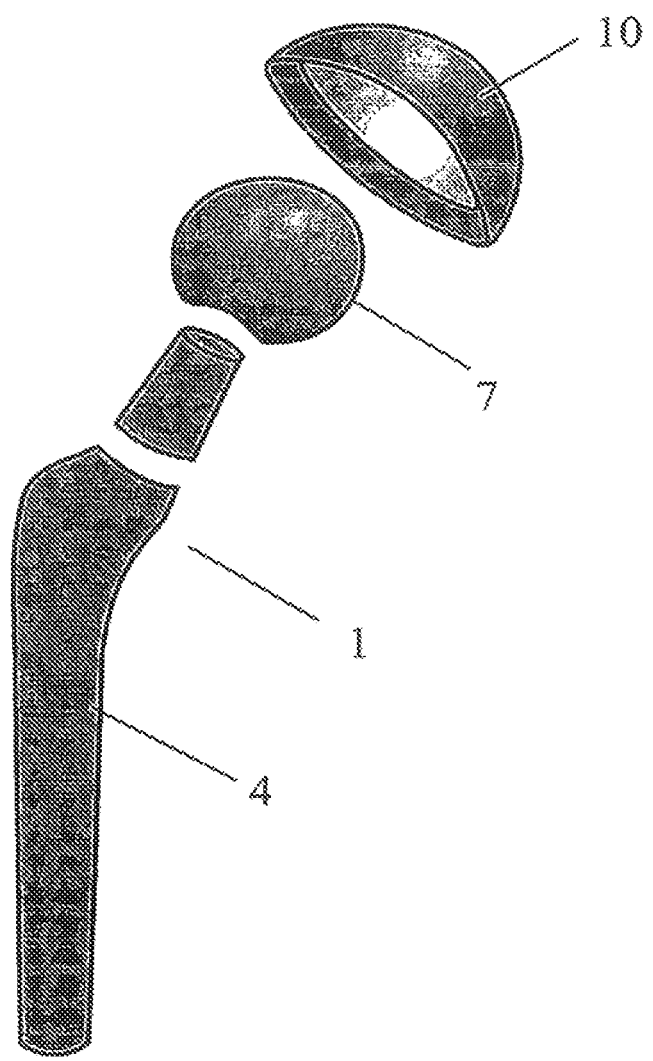
FIG. 5 illustrates an example of a total hip replacement prosthesis.

FIG. 5 illustrates an example of a total hip replacement prosthesis which consists of (1), a femoral stem (4), femoral head (7), and an acetabular cup (10). The femoral head may be an integral part of the stem or it may be a separate component. The femoral stem s press fit or cemented into the femur for stabilization of the implant. Oftentimes in conventional hip prostheses, wire mesh or beads or roughened surfaces are used to enhance fixation stability of hip prostheses. Nevertheless, further improvements in the total design of hip prosthesis are required to assure stable fixation of the implanted prosthesis at the bone/metal interface. Thus, in cemented prosthetic devices there has not been satisfactory fixation due to the various stress loads; i.e., compression, shear and torsion, to which the implanted device is subjected. These mechanical forces, especially shear and torsion, weaken fixation at the bone-cement and/or cement-implant interface. In addition, it is known that there is a tendency for bone resorption which also weakens the cement bond between the bone and the implant. An example it the interface between the intramedullary canal of the femur, and the femoral prosthesis. By providing a bone ingrowth surface on the prosthetic device a more stable fixation would be expected and some advances along these lines have been made. However, bone ingrowth requires the prosthesis to be stably fixed without movement for at least six weeks and any relative motion of the prosthesis during that period prevents or minimizes bony ingrowth.

Figure 6:
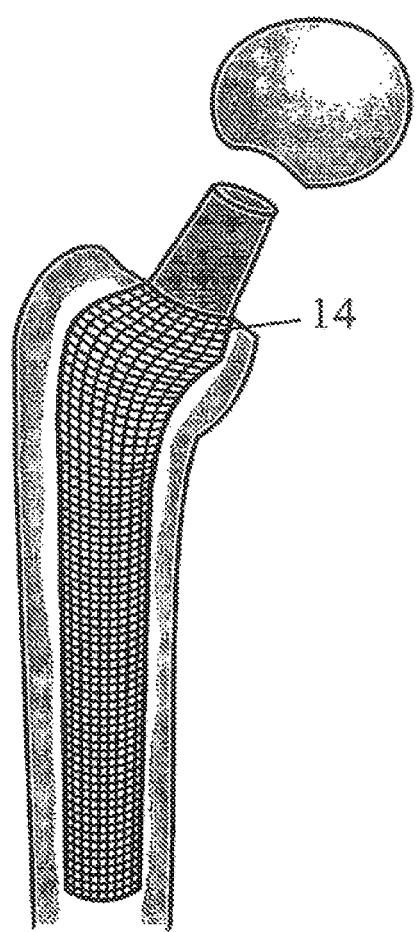
FIG. 6 illustrates a hip prosthesis employing a mesh-tissue integration implant component as a femoral stem.

Any and all of the surfaces of the implant which form interfaces with bone tissue may be comprised of the fenestrated shell component of the present invention and would result in a stronger union. For example, loosening commonly occurs between the implanted femoral stem and the femur. Replacing the conventional solid femoral stem with a fenestrated shell component is but one aspect of the present invention. Presently, the implant is fixated with bone cement and/or is press fit into place. FIG. 6 illustrates a hip prosthesis employing an MTII component as a femoral stem (acetabular cup component not shown). The fenestrations (14) appear on the femoral stem in this example, however, a MTII hip prostheses may be designed having fenestrations elsewhere as well, such as on the outside of the acetabular cup (not shown). Also in accordance with the present invention, a biologic core may be located within and/or in-between the fenestrated shell(s). Within weeks of implantation, bone ingrowth would act as an anchor for the shell to the bone, increasing fixation. In this way, the fixation stability, although sufficiently strong at the outset to allow for a rapid recovery period, would be weakest upon or shortly after implantation, but would strengthen gradually and continuously as the implant ages. The biologic core may include any one or a combination of substances, materials, or factors that promote bone or tissue growth. This could be, for example, bone morphogenetic protein, or any factor that can enhance bone growth. Preferably, the biologic core comprises bone graft or biologically active bone graft substitutes. Where bone is used, it may originate from a variety of sources, including autogenous bone material, allografts, or xenografts. Additionally, the biologic core may comprise other therapeutic agents, such as pharmaceutical components.

Figure 7:
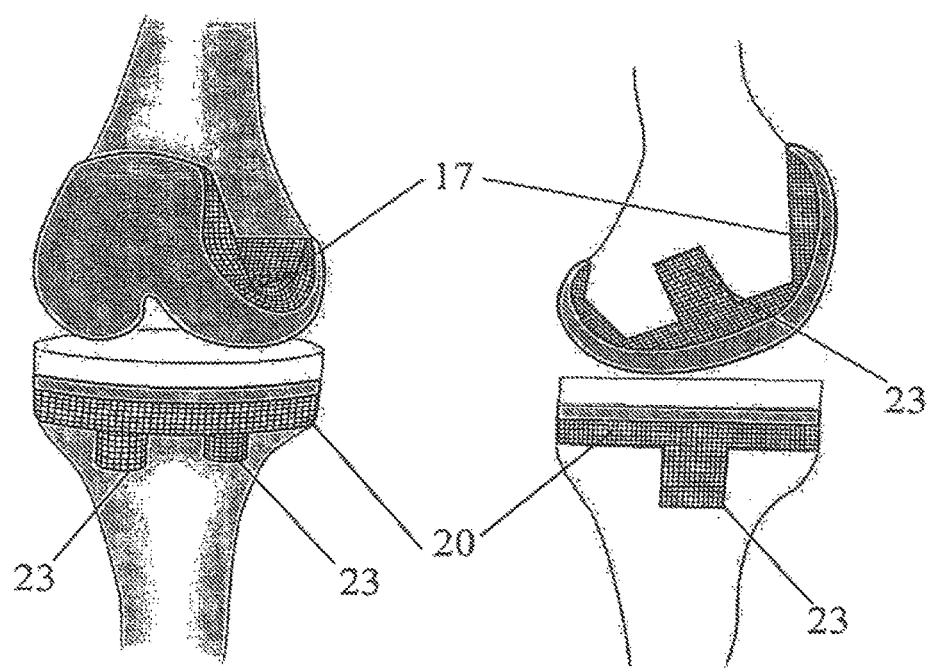
FIG. 7 illustrates an example of a knee prosthesis employing mesh-tissue integration implant components.

FIG. 7 shows a knee prosthesis employing MTII components on various surfaces; in this example they appear on the bone-adjoining surfaces of the femoral component (17) and the tibial base (20). Like the MTII hip prosthesis, more or less of the total surface area of the prosthesis may comprise MTII modifications. Typically, conventional knee prostheses are affixed in place by press fining of the posts and cementing or the remainder of those prostheses surfaces which contact bone. Applying the present invention to the knee prostheses, one or more of the surfaces which contact bone may comprise an MTII component. This could include the pegs (23) on either or both of the femoral or tibial components. Similar to the hip prosthesis discussed above, a biologic core may be located within and/or in-between the fenestrated shell(s). Like the hip prosthesis, the implant fixation would be weakest upon or shortly after implantation, but would steadily strengthen as the implant ages. The biologic core may again include any one or a combination of substances, materials, or factors that promote bone or tissue growth. This could be, for example, bone morphogenetic protein, or any factor that can enhance bone growth. Preferably, the biologic core comprises bone graft or biologically active bone graft substitutes. Where bone is used, it may originate from a variety of sources, including autogenous bone material, allografts or xenografts. Additionally, the biologic core may comprise other therapeutic agents, such as pharmaceutical components.

Figure 8:
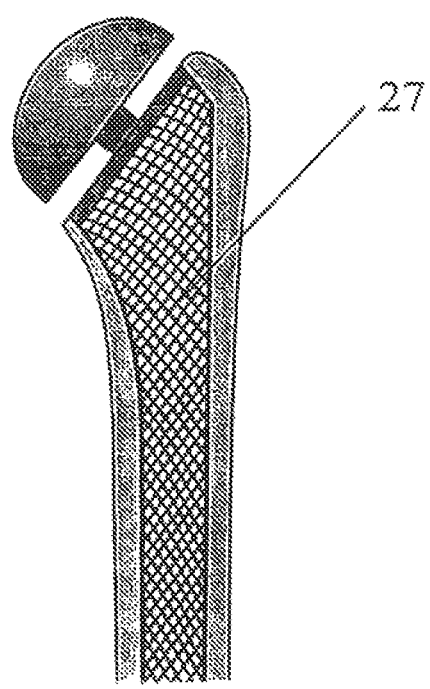
FIG. 8 illustrates an example of a shoulder prosthesis employing mesh-tissue integration implant components.

A shoulder prosthesis employing MTII components is shown in FIG. 8. In the example shown, the surface area (27) of the implant directly contacting the humerus consists of the MTII. As with the hip and knee prostheses, more or less of the total surface area of the prosthesis may comprise MTII modifications. Application of the present invention to improve fixation stability in an implanted shoulder prosthesis could be accomplished by replacing one or more of the bone-contacting surfaces of the prosthesis with MTII components. These surfaces include that of the glenoid component (including the various pins present on this component) and the humeral stem component. The biologic core, as described for the hip and knee prostheses, is also useful for shoulder prostheses, working in conjunction with the fenestrated shell component to promote integration with surrounding tissue such that a seamless union results.

The present invention has application for other joint prostheses. In addition to hip, knee and shoulder prostheses, it is also applicable to ankle, wrist, elbow, finger, foot, and toe prostheses. This list is merely illustrative and not exhaustive and the skilled artisan recognizes other possibilities.

Vertebral disk prostheses are also candidates for application of the present invention. Disk implants are particularly amenable to the use of the present invention, as a high degree of integration between the implant and the bone is desirable in such applications.

Intramedullary or extramedullary nails are also candidates for applications of the present invention. These would include be not be limited to intramedullary nulls for fracture fixation, bone reinforcement, bone reconstruction, extracorporeal prosthesis, rods, screws, plates, and related and similar devices for the bone reinforcement and reconstruction.

Figure 9:
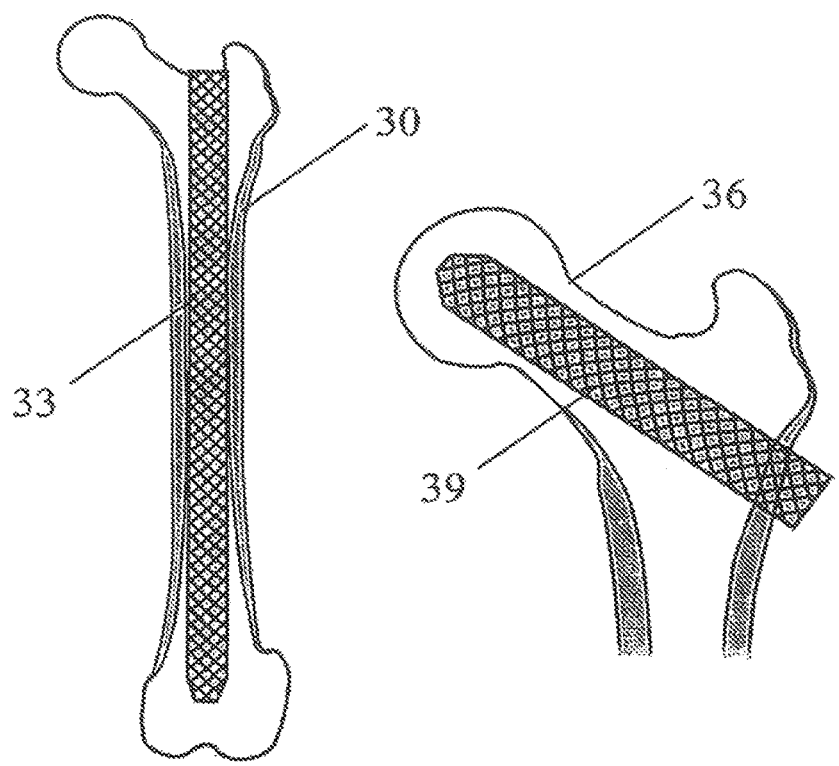
FIG. 9 illustrates the use of the device as a reinforcement for an entire femur (left), and for a proximal portion of the femur (right).

Another embodiment of the MTII or a fenestrated shell component is as a reinforcement for bone. This embodiment is a form of intramedullary nail and/or transosseous pin or insert that can also be used for the reinforcement of osteoporotic and/or osteopenic bone as fracture prophylaxis. When used prophylatically, the device is useful for the prevention of musculo-skeletal problems, i.e., fractures, which may result from osteoporosis or other conditions of weakened bone stock or weakened bone biomechanics. Alternatively, it may be used as a treatment in the same way that conventional nails or pins are presently used. The MTII design can provide mechanical stability that is compatible with the host bone. Additionally, this device can enhance host hone biology by providing bone graft, growth factors, and/or or other medications that can be placed in the core of MTII. The MTII can be used to reinforce the bone throughout its entire length or be used for a designated portion of bone anatomy such as the femoral neck. FIG. 9 provides a schematic illustration of this embodiment. On the left side of FIG. 9 there is a femur (30) in which there is implanted an implant a device (33) which could be a fenestrated shell component or an MTII. The right side of FIG. 9 illustrates the use of the device (39) in reinforcing the femoral neck (36). The fenestrated shell component or MTII (39) may have threads to secure it into the bone.

Although the foregoing focuses on hip, knee, ankles, foot, toe, shoulder, elbow, wrist, and finger prostheses, it should be understood that the present invention is not so limited and may be applied to any and all orthopaedic implants. The degree of integration realized when utilizing the present invention is improved for any such prosthetic device. Press-fit and cemented fixations are, by their very nature, strongest at or shortly after implantation. For a press-fit implantation, the fixation is greatest before the cumulative effect of normal biomechanical loads and other forces begin to affect the implant. The situation is analogous for cemented bone implants. In this case, aging of the cement is also n factor weakening the fixation of the cemented implant. Regardless of the nature of the prosthesis, it is always desirable to realize an improvement in fixation over time, as the implant ages.

The nature of the fenestrations (for example, the size, geometry and number) can be manipulated to provide for more seamless integration of the resulting implant. For example, the geometry of the fenestrations maybe varied according to the characteristics of the bone at the implant site. Denser and thicker bone in the implant area may allow for a smaller number of larger fenestrations, while a lesser bone density or a thinner bone benefits from a larger number of smaller fenestrations. Areas of mixed density/thickness may benefit from an implant having inhomogeneity with regard to the number and geometry of fenestrations.

The material comprising the fenestrated shell component may be titanium, stainless steel, their alloys, ceramic cobalt-chromium, or any other biocompatible material currently available or discovered or developed in the future. It is also possible to apply the present invention to orthopaedic implant comprising composite materials. These materials consist of a homogeneous surface layer and one or more substrate layers.

The biologic core also serves to improve the degree of integration between the implant and the surrounding tissue. The choice of material for the biologic core is not limited, but it is preferable to choose a material that enhances bone growth and promotes ingrowth and ongrowth between the native surrounding bone and the implant. The ingrowth and ongrowth occurs through the fenestrations in the outer and/or inner shell of the implant. The presence of the fenestrations allows for physical contact between the biological core material, the fenestrated shell(s), and surrounding tissue, thereby permitting a union between any two or all three of these domains. The presence of the fenestrations allows for physical contact between the biological core material, the shell, and surrounding tissue, thereby permitting a union between any two or all three of these domains.

One possible example of material for the biologic core includes bone. Either autogenous bone or bone allografts can be used. In the case of allografts, cadaver bone may be used. Synthetic materials that mimic bone material, such as apatite and its derivatives may also be used. It is also envisioned that bone replacement materials yet to be developed would be useful as biologic core materials for the present invention.

As an alternative or in addition to, bone and bone-like materials, it is possible that biologically active substances that promote bone growth may be useful as biologic core materials in the present invention. Bone morphogenetic protein (BMP) is one example of such a bone growth-producing substance. Any (actor that promotes bone growth, used alone or with bone or bone-like material or other materials, is a possible embodiment of the present invention. This includes the use of such factors immobilized onto a solid support placed in the interior of the fenestrated shell(s). The configuration of the instant implant (fenestrated outer and/or inner shell housing a biologic core) permits the utilization of materials enhancing bone healing, including those materials that possess less than optimal structural properties but superior biologic activity. The configuration of the instant implant (fenestrated outer shell housing a biologic core) permits the utilization of materials enhancing bone healing, including those materials that possess less than optimal structural properties but superior biologic activity.

Although the specific examples discussed above focus on joint implants, the MTII can be configured to all other bone implants. The flexibility of the invention allows for the option of intramedullary, extramedullary, juxta-osseous, or transosseous implantation. This flexibility allows the MTII to be used as a stand alone treatment device or in conjunction with both currently existing and yet-to-be developed hone therapies. The fenestrated outer and/or inner shell can be customized for specific applications, by modifying one or more physical parameters. These include, but are not limited to, overall size, thickness of the shell wall, the number, geometry and size of the fenestrations, the geometry of the shell itself (including, e.g., the presence of absence of a taper). The MTII, because of this flexibility, provides immediate restoration of function rather than local limb anatomy, and can be configured to conform to local host bone biomechanics.

The use of the implant of the present invention for mesh-bone integration implants utilizes all of the previously discussed advantages afforded by the MTII and are considerably superior in quality of fixation and longevity to conventional orthopaedic implants. Better bonding with the host bone is realized through minimizing the interface, enhancing tissue ingrowth, and improving biomechanical and biological characteristics and properties of the implant. Superior biomechanical properties are realized through the use of a less bulky and stiff implant, lessening any biomechanical disparity which can result in stress risers, stress shielding and bone atrophy. The judicious use of a biologic core which supports host bone biology allows for the application of biologic factors which could further enhance implant function. By occupying less space, the present implant alters the local tissue biology to a lesser extent than conventional implants. Therefore, biological and biomechanical disparities between the implant and the host tissue are diminished or eliminated as compared to conventional implants, resulting in significant improvements in implant function and longevity. In contrast to conventional implants which often exhibit maximal fixation at, or shortly after, implantation but suffer from a loss of fixation as time passes, the implants of the present invention enjoy increasing fixation as they age. This is because the implant becomes progressively more integrated into the host bone.

Figure 10:
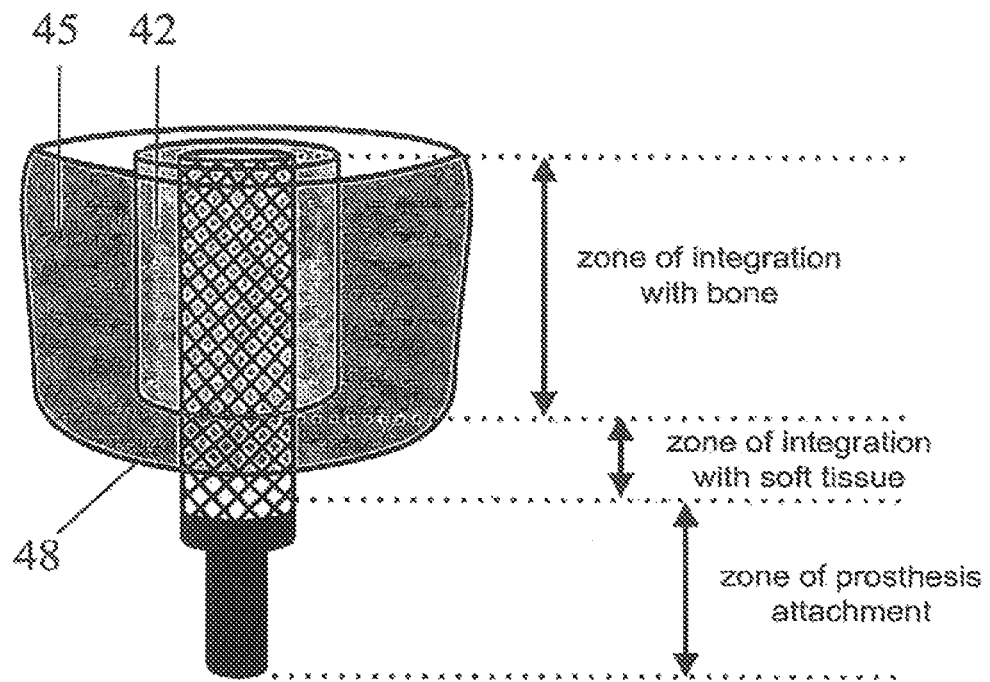
FIG. 10 illustrates one example of the basic design of the extracorporeal embodiment of the mesh-tissue integration implant.

Although the implant and method of the present invention has been described as being internally implanted intramedullary, extramedullarly, juxta-osseously, transosseously, or any combination thereof, it is also within the scope of the present invention that the implant in some instances may comprise an extracorporeal prosthesis portion. For example, an embodiment may include a mesh directly implanted in the bone, but also having a portion that protrudes from the bone and protrudes outside of the body. One non-limiting example of this is useful in below knee amputations. The mesh implant could be anchored in remaining bone with a portion of it protruding out of the body and being capable of attaching to (either integrally or non-integrally) or cooperating with, a leg prosthesis serving as a surrogate for the amputated portion of leg. FIG. 10 illustrates one example of the basic design of the extracorporeal embodiment. It comprises a zone of integration with bone (42) which is analogous to the purely intracorporeal embodiments discussed above. It also comprises a zone of integration with soft tissue in which it is in contact with muscles (45), skin (48), or other soft tissue. Finally, it also comprises a zone of prosthesis attachment, in which another extracorporeal device may be attached. This extracorporeal device may be an artificial limb. It may also be an artificial tooth in which case the entire device comprises a dental implant. The skilled artisan will recognize the other possibilities which are also within the scope of the invention. Any configuration is possible for this embodiment, so long as the mesh implant comprises an extracorporeal prosthesis portion.

The implants of the present invention may also be modified by coating of their surfaces. For example, a coating of hydroxyapatite could cover at least a part of the surface of the MTII implant. Other coating materials known in the art may also be used. These materials can be used to further promote integration of the implant with surrounding tissue and improvement of fixation.

The present invention also includes a method for making a variety of implants designs characterized by the presence of a fenestrated hollow shell and a biological core. The fenestrations are located in a shell component which has been specifically chosen and manufactured to the dimensions necessary for a particular application. The biological core is then placed within the outer shell at some time prior to, or simultaneously to, implantation.

The implants of the present invention can be used in conjunction with current therapeutic methods similar to conventional orthopaedic implants. This includes, but is not limited to, intramedullary, extramedullary, juxta-osseous, and transosseous implant fixation. The present invention can be used to design implants for joint replacement, fracture fixation, bone reinforcement, and bone reconstruction.

One skilled in the art readily appreciates that the patent invention is well adapted to carry out the objectives and obtain the ends and advantages mentioned as well as those inherent therein. Materials, reactions, sequences, methods, procedures and techniques described herein are presently representative of the preferred embodiments and are intended to be exemplary and are not intended as limitations of the scope. Changes therein and other uses will occur to those skilled in the art which are encompassed within the spirit of the invention or defined by the scope of the pending claims.

What is claimed is:

1. A musculo-skeletal implant comprising a first end having a vertebral-contacting surface to contact a first vertebra, a second end having a vertebral-contacting surface to contact a second vertebra, a longitudinal axis extending through respective centers of the first and second ends, an outer fenestrated wall extending from the first end to the second end, and a monolithic inner fenestrated wall inside the outer fenestrated wall and extending entirely around the longitudinal axis to laterally surround a central hollow cavity that extends through the first and second ends, wherein an open space extends through the first and second ends and between the inner fenestrated wall and the outer fenestrated wall from the first end to the second end, wherein fenestrations of the outer fenestrated wall extend toward the inner fenestrated wall and into the open space, wherein fenestrations of the inner fenestrated wall are arranged laterally around the longitudinal axis, wherein the open space extends through the first end to an outside of the implant via a plurality of individual openings each forming a shape with a different number of sides than at least one of the fenestrations of the inner or outer fenestrated walls, and wherein at least one linear pathway extends unobstructed from the hollow cavity through respective fenestrations of the inner and outer fenestrated walls to the outside of the implant, wherein the inner fenestrated wall is integrally connected with the outer fenestrated wall by a plurality of interconnecting members, wherein first ones of the interconnecting members located at an end face at the first end at least partially define the individual openings and have at least a portion that faces away from all other parts of the implant, while another one of the interconnecting members is spaced apart from the first and second ends, wherein at least two of the interconnecting members are aligned laterally around the longitudinal axis, and wherein a distance between the inner and outer fenestrated walls at one of the interconnecting members is substantially the same as a distance between the inner and outer fenestrated walls at a location between two laterally adjacent ones of the interconnecting members, and wherein the inner and outer fenestrated walls comprise a non-biodegradable material and are permanently fixable with a host body tissue by integration as a structural support of the inner and outer fenestrated walls therewith.

2. The musculo-skeletal implant of claim 1, wherein the implant comprises at least one of titanium or a titanium alloy.

3. The musculo-skeletal implant of claim 1, wherein the musculo-skeletal implant is a vertebral implant.

4. The musculo-skeletal implant of claim 1, wherein the interconnecting members are oriented substantially in a radial direction transverse to the longitudinal axis.

5. The musculo-skeletal implant of claim 1, wherein at least one of the interconnecting members is located substantially equidistant between the first end of the implant and the second end of the implant.

6. The musculo-skeletal implant of claim 1, wherein the fenestrations of the outer fenestrated wall are diamond shaped.

7. The musculo-skeletal implant of claim 1, wherein the outer fenestrated wall and the inner fenestrated wall are configured to concurrently contact a vertebra at the first end of the implant and to contact an adjacent vertebra at the second end of the implant.

8. The musculo-skeletal implant of claim 1, wherein some of the interconnecting members are spaced apart axially from one another at a regular interval.

9. The musculo-skeletal implant of claim 1, wherein the inner fenestrated wall and the outer fenestrated wall extend coaxially.

10. The musculo-skeletal implant of claim 1, wherein the open space between the inner fenestrated wall and the outer fenestrated wall is filled with bone material.

11. The musculo-skeletal implant of claim 1, further comprising a biologic core within the outer fenestrated wall.

12. The musculo-skeletal implant of claim 1, wherein the inner fenestrated wall is positioned completely within the outer fenestrated wall.

13. The musculo-skeletal implant of claim 1, wherein the outer fenestrated wall is exposed to permit contact with body tissue.

14. The musculo-skeletal implant of claim 1, wherein at least one of the plurality of individual openings is formed at the first end of the implant.

15. The musculo-skeletal implant of claim 1, wherein at least part of the inner or outer fenestrated walls is curved.

16. The musculo-skeletal implant of claim 1, wherein at least one interconnecting member that defines the at least one linear pathway extends along a straight line from the inner fenestrated wall to the outer fenestrated wall.

17. The musculo-skeletal implant of claim 1, wherein the outer fenestrated wall comprises at least one portion that extends continuously from the first end of the implant to the second end of the implant at a constant angle relative to a plane in which the end face at the first end extends.

18. The musculo-skeletal implant of claim 1, wherein two fenestrations of the outer fenestrated wall are directly adjacent to one another and axially offset from one another, with each having top and bottom ends spaced apart from the longitudinal axis by substantially the same distance.

19. A musculo-skeletal implant comprising first and second ends each having a vertebral-contacting surface configured to contact respective vertebrae, a longitudinal axis extending through respective centers of the first and second ends, an outer fenestrated wall extending from the first end to the second end, and a monolithic inner fenestrated wall inside the outer fenestrated wall and extending entirely around the longitudinal axis to laterally surround a central hollow cavity that extends through the first and second ends, the outer and inner fenestrated walls each comprising a non-biodegradable material, wherein the inner fenestrated wall is integrally connected with the outer fenestrated wall by a plurality of interconnecting members, wherein first ones of the interconnecting members located at an end face at the first end each has at least a portion that faces away from all other parts of the implant, while another one of the interconnecting members is spaced apart from the first and second ends, wherein a first fenestration of the outer fenestrated wall and a first fenestration of the inner fenestrated wall form respective polygons with a same number of sides, such that a linear pathway having a shape corresponding to the respective polygons extends unobstructed from the hollow cavity through the respective first fenestrations of the inner and outer fenestrated walls to an outside of the implant, and wherein an open space extends between the inner and outer fenestrated walls and through the first and second ends, the open space extending through the first end to the outside of the implant via a plurality of individual openings that are at least partially defined by the first ones of the interconnecting members, each individual opening forming a shape with a different number of sides than the respective polygons formed by the first fenestrations of the inner and outer fenestrated walls.

20. The musculo-skeletal implant of claim 19, wherein the implant comprises at least one of titanium or a titanium alloy.

21. The musculo-skeletal implant of claim 19, wherein the musculo-skeletal implant is a vertebral implant.

22. The musculo-skeletal implant of claim 19, wherein the interconnecting members are oriented substantially in a radial direction transverse to the longitudinal axis.

23. The musculo-skeletal implant of claim 19, wherein at least one of the interconnecting members is located substantially equidistant between the first end of the implant and the second end of the implant.

24. The musculo-skeletal implant of claim 19, wherein the first fenestration of the outer fenestrated wall is diamond shaped.

25. The musculo-skeletal implant of claim 19, wherein the outer fenestrated wall and the inner fenestrated wall are configured to concurrently contact a vertebra at the first end of the implant and to contact an adjacent vertebra at the second end of the implant.

26. The musculo-skeletal implant of claim 19, wherein the open space between the inner fenestrated wall and the outer fenestrated wall is filled with bone material.

27. The musculo-skeletal implant of claim 19, wherein the open space between the inner fenestrated wall and the outer fenestrated wall extends to the second end of the implant.

28. A musculo-skeletal implant comprising a first end having a vertebral-contacting surface to contact a first vertebra, a second end having a vertebral-contacting surface to contact a second vertebra, a longitudinal axis extending through respective centers of the first and second ends, an outer fenestrated surface extending from the first end to the second end and facing outward and a monolithic inner fenestrated surface inside the outer fenestrated surface and facing inward, the inner and outer fenestrated surfaces extending entirely around the longitudinal axis to laterally surround a central hollow cavity that extends longitudinally through the first and second ends, wherein a plurality of individual openings extend longitudinally through the first and second ends and entirely through the implant between and spaced apart from the inner and outer fenestrated surfaces, wherein fenestrations of the outer fenestrated surface extend toward the inner fenestrated surface and into respective openings of the plurality of individual openings, wherein fenestrations of the inner fenestrated surface are arranged laterally around the longitudinal axis, wherein at least one of the plurality of individual openings forms a shape at the first end of the implant that has a different number of sides than at least one of the fenestrations of the inner or outer fenestrated surfaces, and wherein at least one linear pathway extends unobstructed from the hollow cavity through respective fenestrations of the inner and outer fenestrated surfaces to an outside of the implant, wherein the inner and outer fenestrated surfaces are integrally connected by a plurality of interconnecting members, wherein first ones of the interconnecting members located at an end face at the first end at least partially define the individual openings and have at least a portion that faces away from all other parts of the implant, while another one of the interconnecting members is spaced apart from the first and second ends, wherein at least two of the interconnecting members are aligned laterally around the longitudinal axis, and wherein a distance between the inner and outer fenestrated surfaces at one of the interconnecting members is substantially the same as a distance between the inner and outer fenestrated surfaces at a location between two laterally adjacent ones of the interconnecting members, and wherein the inner and outer fenestrated surfaces and the interconnecting members comprise a non-biodegradable material and are permanently fixable with a host body tissue by integration as a structural support.

* * * * *